United States Patent
Iyer et al.

(10) Patent No.: US 9,925,707 B2
(45) Date of Patent: Mar. 27, 2018

(54) PROCESS FOR PREPARATION OF BIODEGRADABLE BIOCOMPOSTABLE BIODIGESTIBLE POLYOLEFINS

(71) Applicant: PEP LICENSING LIMITED, Hong Kong (CN)

(72) Inventors: Ravi Srinivasan Iyer, Nagpur (IN); Narinder Bharj, Nagpur (IN); Ammanamanchi Radhakrishna, Nagpur (IN)

(73) Assignee: Pep Licensing Limited, Hong Kong (CN)

( * ) Notice: Subject to any disclaimer, the term of this patent is extended or adjusted under 35 U.S.C. 154(b) by 0 days.

(21) Appl. No.: 14/978,860

(22) Filed: Dec. 22, 2015

(65) Prior Publication Data
US 2017/0175146 A1    Jun. 22, 2017

(51) Int. Cl.
| | | |
|---|---|---|
| *D06P 1/52* | (2006.01) |
| *C08L 89/00* | (2006.01) |
| *C08H 1/00* | (2006.01) |
| *A61K 47/48* | (2006.01) |
| *C10L 1/16* | (2006.01) |
| *B29D 11/00* | (2006.01) |
| *C09K 19/00* | (2006.01) |
| *C10M 111/04* | (2006.01) |
| *B29C 47/00* | (2006.01) |
| *B29C 49/00* | (2006.01) |
| *C12P 5/02* | (2006.01) |
| *B29C 64/106* | (2017.01) |

(52) U.S. Cl.
CPC .......... *B29C 47/0004* (2013.01); *B29C 49/00* (2013.01); *B29C 64/106* (2017.08); *C12P 5/02* (2013.01)

(58) Field of Classification Search
CPC ... B29C 49/00; B29C 47/0004; B29C 64/106; C12P 5/02
USPC ........ 523/124; 524/23; 526/238.1; 525/54.1; 585/10; 264/1.29, 2.5; 428/1.55, 1.33; 508/131
See application file for complete search history.

(56) References Cited

U.S. PATENT DOCUMENTS

| | | | | |
|---|---|---|---|---|
| 3,907,726 A * | 9/1975 | Tomiyama | ........... | C08K 5/0033 |
| | | | | 260/DIG. 43 |
| 4,021,388 A | 5/1977 | Griffin | | |
| 4,133,784 A | 1/1979 | Otey et al. | | |
| 4,337,181 A | 6/1982 | Otey et al. | | |
| 4,931,488 A * | 6/1990 | Chiquet | ............... | C08K 5/0033 |
| | | | | 523/126 |
| 5,281,681 A | 1/1994 | Austin | | |
| 5,316,847 A * | 5/1994 | Suominen | ........... | A01G 13/0275 |
| | | | | 106/215.4 |
| 5,446,078 A * | 8/1995 | Vaidya | ..................... | C08B 31/00 |
| | | | | 523/124 |
| 5,461,094 A | 10/1995 | Yoo et al. | | |
| 5,496,895 A * | 3/1996 | Chinnaswamy | .......... | C08L 3/10 |
| | | | | 525/326.1 |
| 6,987,138 B2 * | 1/2006 | Tokiwa | .................. | C08L 67/04 |
| | | | | 524/17 |

FOREIGN PATENT DOCUMENTS

| | | | | |
|---|---|---|---|---|
| EP | 3 162 841 A1 * | 5/2017 | ................ | C08J 3/20 |
| KR | 90-006336 | 8/1990 | | |
| KR | 91-008553 | 10/1991 | | |

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Seffernick et al., Melamine deaminase and Atrazine chlorohydrolase: 98 percent identical but functionally different. J. Bacteriol., 2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Azevedo et al., Whey protein isolate biodegradable films: influence of citric acid and montmorillonite clay nanoparticles on physical properties. Food Hydrocolloids, 2015, vol. 43: 252-258.*
de Castro et al., Improving the functional properties of milk proteins: focus on the specificities of proteolytic enzymes. Curr. Opin. Food Sci., 2015, vol. 1: 64-69.*
Samarasekara et al., Effect of papain on the biodegradability of polyethylene modified by chitosan. Abstract only, 14th ERU Symposium, 2008: Faculty of Engineering, University of Moratuwa.*
Standard Specification for Compostable Plastics, D6400-99 (ASTM International 1999).
Standard Test Method for Determining Aerobic Biodegradation in Soil of Plastic Materials or Residual Plastic Materials After Composting, D5988-03 (ASTM International 2003).
Packaging—Requirements for packaging recoverable through composting and biodegradation—Test scheme and evaluation criteria for the final acceptance of packaging, BS EN 13432:2000 (BSI Group/CEN 2000).

(Continued)

*Primary Examiner* — Ganapathirama Raghu
(74) *Attorney, Agent, or Firm* — Rosenberg, Klein & Lee

(57) ABSTRACT

This invention relates to a process for preparation of biodegradable biocompostable biodigestible PEPlene polymer (polyolefins) comprising steps of:
 Mixing at least one peptide with at least one protein and enzyme,
 Adding a composting agent,
 Blending with at least one polymer in presence of additive to obtain said PEPlene polymer (polyolefins) material.

7 Claims, 5 Drawing Sheets

(56) References Cited

OTHER PUBLICATIONS

Determination of the ultimate aerobic biodegradability of plastic materials under controlled composting conditions—Method by analysis of evolved carbon dioxide—, ISO 14855-1:2005(E) (ISO 2005).
Plastics, Determination of the ultimate aerobic biodegradability in soil by measuring the oxygen demand in a respirometer or the amount of carbon dioxide evolved, ISO 17556:2003 (ISO 2003).
Standard Guide for Waste Reduction, Resource Recovery, and Use of Recycled Polymeric Materials and Products, D7209-06 (ASTM International 2006).
Plastics—Recycled Plastics—Characteristics of plastic wastes, English Version of DIN EN 15347:2008-02 (CEN 2007).

* cited by examiner

PROCESS FOR PREPARATION OF BIODEGRADABLE BIOCOMPOSTABLE BIODIGESTIBLE POLYOLEFINS

BACKGROUND OF THE INVENTION

1. Field of the Invention

This invention relates to a biodegradable biocompostable biodigestible plastic and a process for preparation thereof.

2. The Related Arts

Plastics are manufactured from petroleum namely polyethylene's, polypropylenes, which takes several years to degrade in the environment and therefore pollute water, soil and air.

Environmental degradation of synthetic polymers occurs at varying rates and to varying degrees depending on the characteristics of polymer and its environment. Such degradations are catalyzed by light, heat, air, water, microorganisms, and mechanical forces such as wind, rain, vehicular traffic, etc. Enhancing the stability and/or the degradability of polymers is generally accomplished by additives, changing the polymer backbone, introduction of functional groups, or by blending with appropriate fillers to make the polymer/plastic material from hydrophobic to hydrophilic material. However, many of these techniques for degradation also result in detrimental properties for the polymer products.

Petroleum based synthetic polymers/plastics to overcome the problems and limit of natural material owing to its excellent physical properties, light weight and cost effectiveness, plasticity is one of the modern scientific characteristics established by developing various hydrophilic polymers, especially hydrophilic plastic. However, each country in the present world is preparing for diversified counter measures as pollution problems from numerous plastic products are globally getting serious and it becomes a challenging matter to solve such pollution problems arising out of plastic wastes.

Recycling, incineration and landfill have been mainly used to solve these environmental pollution problems caused by various solid wastes, including plastic. However, disposal of wastes through landfill as well as recycling cannot solve the environmental pollution problems completely owing to its inherent problems.

Accordingly, great interest and studies on development of biodegradable and/or biocompostable plastic which can degrade itself at the life cycle end are increasing recently. The technology on degradable plastic is divided into photodegradable, oxo-degradable, oxo-biodegradable, biodegradable, bio-photodegradable and a combination of photo- and/or oxo and/or biodegradable plastic formulation technologies which are increasing recently on the industrial scale of manufacturing.

While there are many kinds of biodegradable plastic, for example microorganism producing polymers like PHB (poly-β-hydroxybutylate), polymers using microorganism producing biochemical, or polymers having natural polymer like chitin or starch. The problems which are concerned with the present technology about polymers having various additives such as starch have been mentioned and improvements are described in the literature.

U.S. Pat. No. 4,021,388 by G. J. L. Griffin is directed to a process for preparing biodegradable film improved by treating the surface of starch with silane coupling agent to be hydrophobic, but it only increases physical interacting strength a little between matrix resin and starch. However, it has difficulty to solve the problem of degradation in the physical properties of films upon incorporating starch.

While U.S. Pat. Nos. 4,133,784 and 4,337,181 filed by F. H. Otey et. al. of USDA disclose processes for preparing biodegradable films by adding α-starch to ethylene-acrylic copolymer. It has difficulty to generalize for the high price of ethylene-acrylic copolymer and lowering of physical properties of the produced films.

Korean Patent Publication No. 90-006336 and 91-008553 filed by Sunil Glucose Co., Korea are related to processes for increasing physical interacting strength between matrix resin and starch by increasing hydrophobic property of starch or increasing hydrophilic property of matrix resin to increase compatibility with matrix resin and starch.

U.S. Pat. No. 5,281,681A describes photodegradable and biodegradable polyethylene formulation by co-processing ethylene and 2-methylene-1,3-dioxepane (MDOP) to produce terpolymer which exhibits better photodegradability than the copolymer, because the additional carbonyl groups in the polymer cleave upon absorbing light such as sunlight or UV light. The terpolymer can be both photodegradable and biodegradable because both the ester and the carbonyl functionalize.

U.S. Pat. No. 5,461,094A describes biodegradable polyethylene composition chemically bonded with starch and a process for preparing thereof.

Therefore, it is required to provide high yield Peptide-polyethylene herein referred to as PEPlene, having good biodegradability/biocompostability/biodigestion in the environment.

SUMMARY OF THE INVENTION

An object of this invention is to propose a biodegradable biocompostable biodigestible plastic and a process for preparation thereof which overcomes disadvantages associated with the prior arts.

Another object of this invention is to propose a biodegradable biocompostable biodigestible plastic and a process for preparation thereof which improves polymer biodegradability/biocompostability/biodigestion without the loss of physical strength, structural characteristics and also being recyclable in the main recycling stream should the opportunity arise without affecting the stream.

Further object of the present invention is to propose a biodegradable/biocompostable/biodigestible plastic and a process for preparation thereof which is cost effective.

Yet another object of this invention is to propose a biodegradable/biocompostable/biodigestible plastic and a process for preparation thereof which is environment friendly.

The present invention proposes Biodegradable/Biocompostable/Biodigestible plastics or polymer products such as market carry bags, mulch film for agricultural use, packing films etc., to name a few plus replace the normal petroleum source plastics by incorporating biodegradable/biocompostable/biodigestible additives in the polymer processing to render them biodegradable/biocompostable/biodigestible. Thus, a plastic formulation has been developed by incorporating natural peptides/enzyme/protein from edible source to make non-biodegradable petroleum based polymers namely the polyolefin such as polyethylene, polypropylene and their different grades as Biodegradable/Biocompostable/Biodigestible polyolefin polymer.

Thus the present invention describes a biodegradable/biocompostable/biodigestible film prepared by chemical bonding of peptides/enzyme/protein and other additives with an example of polyethylene chains, which is a polyolefin having the most widest general application, and a process for preparing thereof. The same can be the process technology for the other polyolefin's such as polypropylene etc.

BRIEF DESCRIPTION OF THE DRAWINGS

The present invention will be apparent to those skilled in the art by reading the following description of preferred embodiments thereof, with reference to the attached drawings, wherein.

DETAILED DESCRIPTION OF THE PREFERRED EMBODIMENTS

The instant invention makes a disclosure in respect of biodegradable biocompostable biodigestible plastic and a process for preparation thereof.

Accordingly, the Present invention provides a process for composition and composition thereof for accelerating the biodegradation/biocompostability/biodigestion of PEPlene materials.

The process comprises preparing a composition by combing at least one peptide with at least one protein and enzyme, and a composting agent. This is followed by blending with at least one polymer in the presence of additive preferably at a temperature of 45-300° C. so as to retain the essential catalytic properties and nature of the peptides/enzyme/protein.

The composition thus obtained can be directly used or encapsulated in a polymer constituting a coated composition or in liquid form. Various examples of above ingredients can be listed herein below:

Peptide—cellulase, papain, but not restricted to the examples herein.

Protein/enzyme—milk, vegetable. (Soya bean, lady finger). But not restricted to the examples herein.

Composting Agent—carboxy methyl cellulose, hydrolyzed mutton tallow. But not restricted to the examples herein.

Polymer—polyethylene, which can be at least one of linear low density polyethylene (LLDPE), high density polyethylene (HDPE), low density polyethylene (LDPE) medium density polyethylene, ethylene vinyl acetate (EVA) and ethylene butyl acrylate (EBA) and any combination thereof.

Additive—citric acid, lactic acid bacillus, hydrolyzed mutton tallow, yeast and any combination thereof to improve biodegradation/biocompostability/biodigestion properties of polymeric material.

The natural components of the composition of the present invention are food grade materials. This can also include other carbohydrates such as lactose, starch etc.

The present invention leads to reduction in production cost owing to simplification in the process for preparation of the composition. It avoids the problem of degradation in the physical properties of film by enhancing solely physical interacting strength between matrix resin and peptides/enzyme/protein and added additives referred above.

Further according to another embodiment, a biodegradable/biocompostable/biodigestible polyethylene composition can be chemically bonded with starch.

Figure 1:
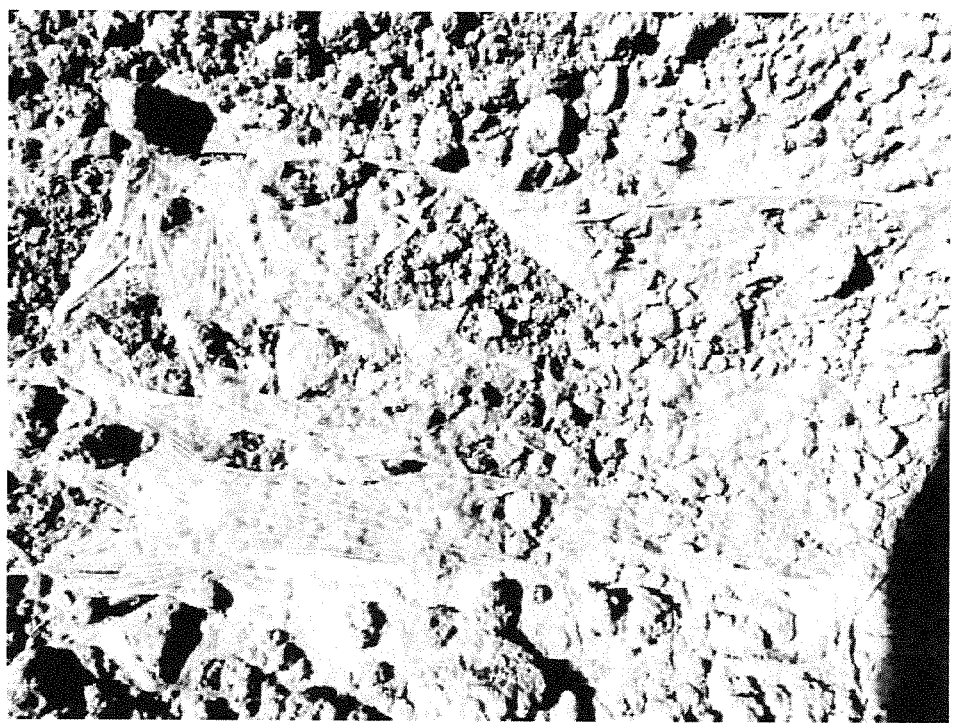
FIG. 1 is an environmental biodegradation of the PEPlene film.

The composition of PEPlene has molecular weight of at least about 7000 with good biodegradable/biocompostable/biodigestible characteristics FIG. 1.

Figure 3:
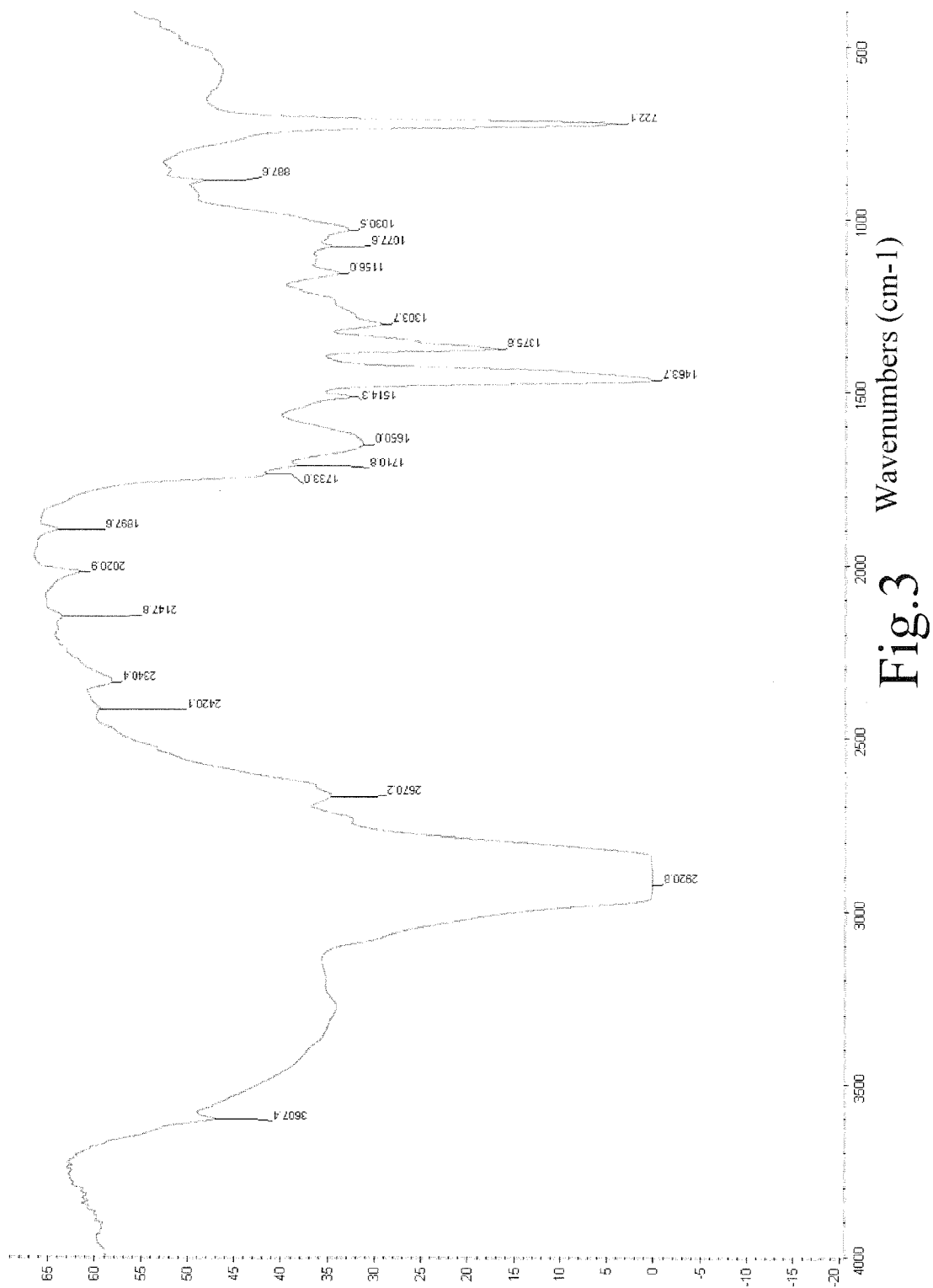
FIG. 3 is a FTIR indicating the peptides/enzyme/protein incorporation in the PEPlene master batch.
Figure 4:
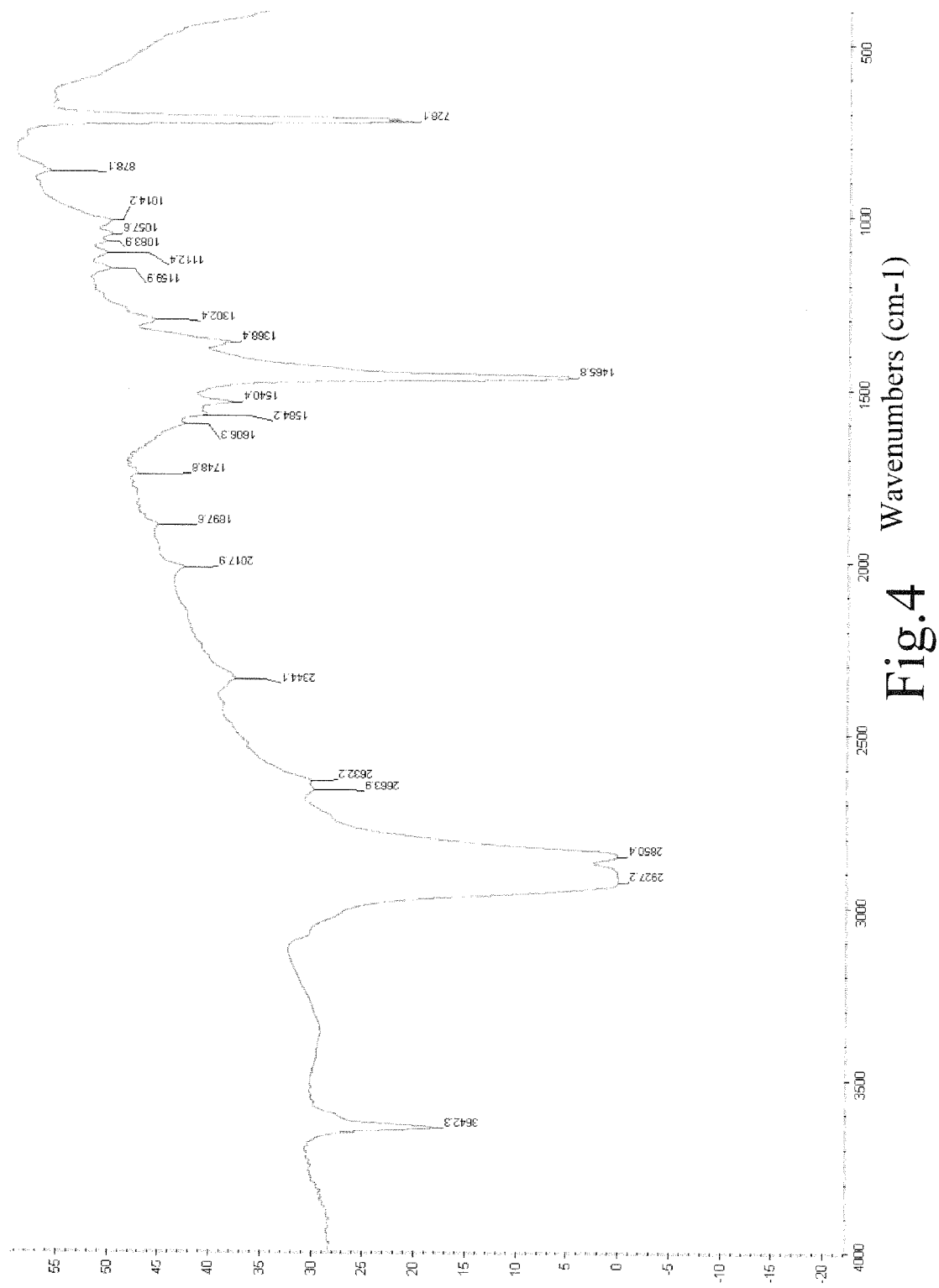
FIG. 4 is a FTIR indicating the peptides/enzyme/protein incorporation in the PEPlene film.

In plastic polymer, x, y and z in space integers of the peptide/enzyme/protein groups such as carboxyl are randomly or uniformly distributed in the polymer along the backbone of the polyethylene polymer, according to the varying concentrations of the functional groups FIGS. 3 and 4.

The blend of plastic composition is subjected to extrusion at a temperature of about 100-350° C. So that during the extrusion process, the composition infuses or penetrates into the cells or molecular structure of the polymer while the polymer is in a pre-molten state. The plastic products obtained from the present process include secondary packaging/plastic films, vest bags, bin liners, rubbish bags, agricultural mulch, and many other types of films. The present blend of composition is also suitable for the polymers e.g. 3D printing, fiber spun, and nonwoven material using injection molding and melted spun process technologies to name a few.

The mechanisms of biodegradation may include the following stages:

Action: Peptide/enzyme/protein help to introduce the hydrophilicity in the chains of the polymer. While the polymer is in the pre-molten state during the process of extrusion the Peptide/enzyme/protein penetrates into the polymer so as to enable the hydrophilicity in the polymer formulation.

Thermal degradation: The hydrophilic nature polymer is processed further into a polymer film which undergoes a thermal degradation or breakdown into smaller fragments, under laboratory conditions this takes place due to temperature conditions and the moisture in the environment and also due to light and oxygen.

Soil action: After thermal degradation (either in laboratory conditions or in the natural environment) the presence of peptide/enzyme/protein in the composition of the present invention due to hydrophilic nature attracts soil microorganisms which attack the polymer. Inherent moisture in the polymer formulation due to hydrophilicity of the composition and/or moisture in the soil (for example 58% moisture) enables the chain links of the polymer, already in a separated or weakened molecular state, to undergo a natural composting process wherein the products of depolymerisation provide nutrients for the soil microorganisms and the remaining products to become biomass.

Degradation: The ultimate products of biodegradation include carbon dioxide and water due to the microbial metabolism of the polymer.

In one example, the enzyme compositions of the present invention are blended with a pulverized co-polymer i.e. LLDPE. Polyethylene used for the manufacturing of films for secondary packaging like vest bags, bin liners, rubbish bags, agricultural mulch films need the co polymer LLDPE both for elasticity and scalability of the film. The presence of peptide/enzyme/proteins and other additives in the polyethylene attracts the soil microorganisms to act on the composted material. The residue is biomass, water and carbon dioxide. However, in the present PEPlene polymer the biodegradation residues are carbon dioxide and water.

Other products resulting from biodegradation or biorefining include gases (e.g. Methane), Ketones (e.g.

Acetone) and alcohols (e.g. Methanol, Ethanol, Propanol, and Butanol). Products such as Methane and Ethanol are known sources of energy and it is envisaged that these, or other resulting products, may be captured for further use, such as to act as energy sources.

One advantage of the present invention is that the polymer products obtained by the present invention retain the desired mechanical properties and shelf life plus recycling of polymers equal to the non-biodegradable polymer—example polyethylene. Unlike the photo-oxidative or oxodegradable agents which initiate the degradation of the Polymer spontaneously and their-by reduce the shelf life of the polymer products, enzymatically initiated biodegradation/biocompostability/biodigestion process begins only upon exposure to microbes in the environment as life cycle end.

Figure 2:
FIG. 2 is a 150 days environmental soil biodegradation of the PEPlene film.

The PEPlene films prepared using the peptide/enzyme/protein composition either by directly dispersed or encapsulated in the present invention have been successfully tested as per ASTM D 5988, ISO 14855, ISO 17556 and EN 13432/ASTM D6400 (and other national equivalents) test protocols for bio degradability and Eco toxicity and plant germination capability of the soil in which these films biodegrade. For example, EN protocols for cellulose based products require greater than 90% degradation within 180 days. Products according to the present invention start to degrade from 90 days under composting conditions FIGS. 1 and 2. Speed of degradation is generally affected by environmental microbial conditions, the amount of peptide/enzyme/protein composition and the thickness of the product. By way of example, degradation of products prepared according to the present invention has been achieved with extruded film of 5-50 microns thickness.

Accordingly, a further advantage of the present invention is that the compositions comprise natural and food grade materials and leave no toxic residues after biodegradation and/or are within the heavy metal limits as prescribed by various countries for the plastic material/products.

Figure 5:
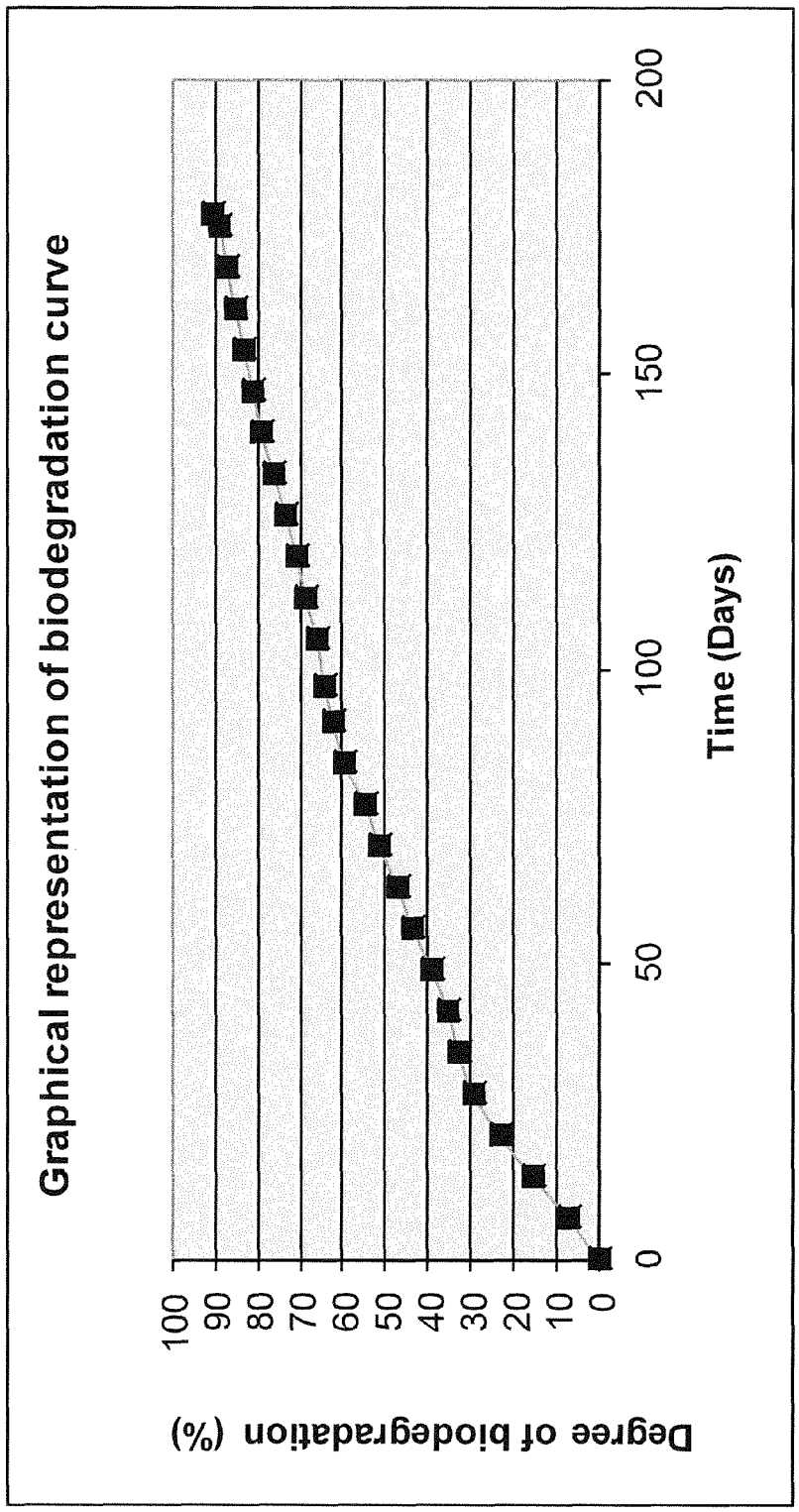
FIG. 5 is a PEPlene percentage degree of biodegradation.

The present invention product is also recyclable in accordance with ASTM D 7209 protocol and EN 15347; The present invention product is also compostable according to standard EN 13432; and biodegradable according to standards ASTM D 5988, ISO 14855, ISO 17556 and EN 13432! ASTM D6400 (and other national equivalents) test protocols for biodegradability FIG. 5.

Also, the present invention evaluated under US FDA 177.1520 for food contact safety compliance.

A further advantage of the present invention is that the materials prepared according to the invention biodegrade when subjected to suitably environmental conditions. The product PEPlene films of the present innovation are also stable until disposal, such as into soil, compost, landfill, bio-digester or the like and under anaerobic conditions. The materials are able to be metabolized into biomass by the colony forming bacterial groups present in the compositions of the present invention and the microorganisms available in the soil.

The compositions of the present invention with polyolefin such as polyethylene under aerobic conditions have shown that it is possible to subject poly films to complete biodegradation and bio-compostable by oxidative microbial attack.

It is to be noted that the present invention is susceptible to modifications, adaptations and changes by those skilled in the art. Such variant embodiments employing the concepts and features of this invention are intended to be within the scope of the present invention, which is further set forth under the following claims.

What is claimed is:

1. A process for preparation of a biodegradable, biocompostable, and biodigestible plastic, comprising the steps of:
   mixing papain with at least one milk protein,
   adding a composting agent containing cellulose or modified cellulose, and
   blending with at least one polyolefin in the presence of an additive selected from citric acid, lactic acid bacillus, hydrolyzed mutton tallow, yeast, and combinations thereof to obtain said plastic.

2. The process for preparation of a biodegradable, biocompostable, and biodigestible plastic as claimed in claim 1, wherein said blending is carried out at a temperature of 45-300° C. to retain the essential catalytic properties and nature of the mixture of papain and milk protein in the solid or liquid form.

3. The process for preparation of a biodegradable, biocompostable, and biodigestible plastic as claimed in claim 1, wherein the composting agent is carboxymethyl cellulose.

4. The process for preparation of a biodegradable, biocompostable, and biodigestible plastic as claimed in claim 1, wherein the polyolefin comprises polyethylene.

5. The process for preparation of a biodegradable, biocompostable, and biodigestible plastic as claimed in claim 1, further comprising the step of:
   subjecting said plastic to extrusion at a temperature of up to 350° C.

6. The process for preparation of a biodegradable, biocompostable, and biodigestible plastic as claimed in claim 1, further comprising the steps of:
   fabricating said plastic into plastic products including at least one of secondary packaging/plastic films, vest bags, bin liners, rubbish bags, agricultural mulch films, polymer fibers, and nonwoven spun materials.

7. The process for the preparation of a biodegradable, biocompostable, and biodigestible plastic as claimed in claim 4, wherein the polyethylene is selected from a group including:
   low density polyethylene (LLDPE),
   high density polyethylene (HDPE),
   low density polyethylene (LDPE),
   medium density polyethylene (MDPE), ethylene vinyl acetate (EVA), ethylene butyl acrylate (EBA), and combinations thereof.

* * * * *